United States Patent [19]
Michelson

[11] Patent Number: 4,709,996
[45] Date of Patent: * Dec. 1, 1987

[54] FLUID LENS

[76] Inventor: Paul E. Michelson, 2280 Calle Tiara, La Jolla, Calif. 92037

[*] Notice: The portion of the term of this patent subsequent to Aug. 21, 2001 has been disclaimed.

[21] Appl. No.: 639,480

[22] Filed: Aug. 10, 1984

Related U.S. Application Data

[63] Continuation-in-part of Ser. No. 432,409, Sep. 30, 1982, Pat. No. 4,466,705.

[51] Int. Cl.$^4$ ............... G02B 1/06; G02C 7/04; A61F 2/16; A61K 9/22
[52] U.S. Cl. ............... 350/418; 351/160 H; 604/893; 604/895; 623/6
[58] Field of Search ............... 350/418, 419; 351/160 R-162; 623/6; 604/893, 895

[56] References Cited

U.S. PATENT DOCUMENTS

| | | | |
|---|---|---|---|
| 2,241,415 | 5/1941 | Moulton | 33/54.5 |
| 2,952,023 | 9/1960 | Rosen | 623/6 |
| 3,416,160 | 8/1965 | Arion | 3/36 |
| 3,641,237 | 2/1972 | Gould et al. | 424/16 |
| 3,710,796 | 1/1973 | Neefe | 128/260 |
| 3,832,458 | 8/1974 | Merrill | 424/19 |
| 3,854,480 | 12/1974 | Zaffaroni | 128/260 |
| 3,952,741 | 4/1976 | Baker | 128/260 |
| 3,995,631 | 12/1976 | Higuchi et al. | 128/260 |
| 4,016,880 | 4/1977 | Theeuwes et al. | 128/260 |
| 4,057,619 | 11/1977 | Higuchi et al. | 604/895 |
| 4,123,408 | 10/1978 | Gordon | 260/29.6 |
| 4,153,349 | 5/1979 | Wichterle | 351/160 H |
| 4,163,608 | 8/1979 | Neefe | 351/160 |
| 4,174,156 | 11/1979 | Glorieux | 350/419 |
| 4,235,236 | 11/1980 | Theeuwes | 128/260 |
| 4,253,199 | 3/1981 | Banko | 623/6 |
| 4,326,525 | 4/1982 | Swanson et al. | 128/260 |
| 4,327,725 | 5/1982 | Cortesa et al. | 604/893 |
| 4,340,054 | 7/1982 | Michaels | 128/260 |
| 4,466,705 | 8/1984 | Michelson | 350/418 |

FOREIGN PATENT DOCUMENTS 32517 7/1981 European Pat. Off. ........ 351/160 H

OTHER PUBLICATIONS

Remington's Pharmaceutical Sciences, 16th Edition, Arthur Osol, Editor, Mack Publishing Co. 1980, pp. 182–193, "Complexation", Chapter 14 by Gennaro.
Physical Pharmacy, 2d Edition, Martin et al., Lea & Febiger, 1969, pp. 325–352, "Complexation", Chapter 13.

*Primary Examiner*—Bruce Y. Arnold
*Assistant Examiner*—Scott J. Sugarman
*Attorney, Agent, or Firm*—Spencer & Frank

[57] ABSTRACT

A device for forming a fluid lens when immersed in a liquid medium. The device includes a semipermeable transparent sheath defining a fully enclosed cavity and having a plurality of pores for permitting a liquid to flow into the cavity, and a hydrophilic polymer array disposed in the cavity, presenting a pressure differential across the sheath when the sheath is immersed in the liquid medium for causing liquid medium to flow into the cavity and to hydrate the array, causing the array to expand and to completely fill the cavity, thereby causing the sheath to expand and to assume a defined lenticular shape, wherein the hydrated array assumes a shape having an outer contour defined by the expanded sheath and constitutes a fluid lens.

13 Claims, 5 Drawing Figures

FIG. 1
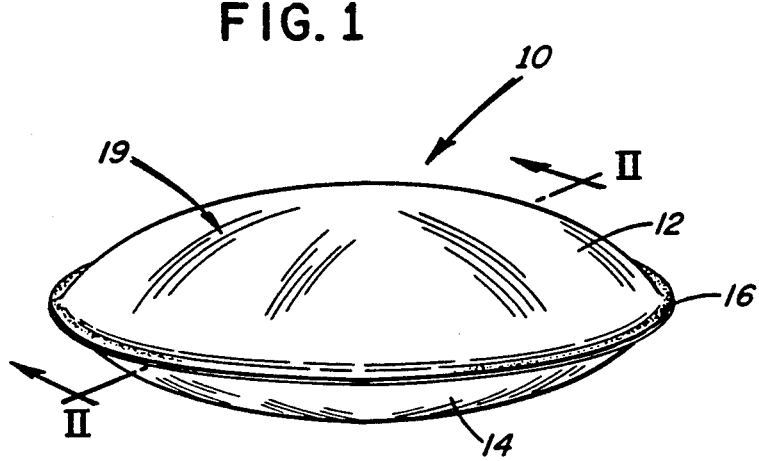
FIG. 2
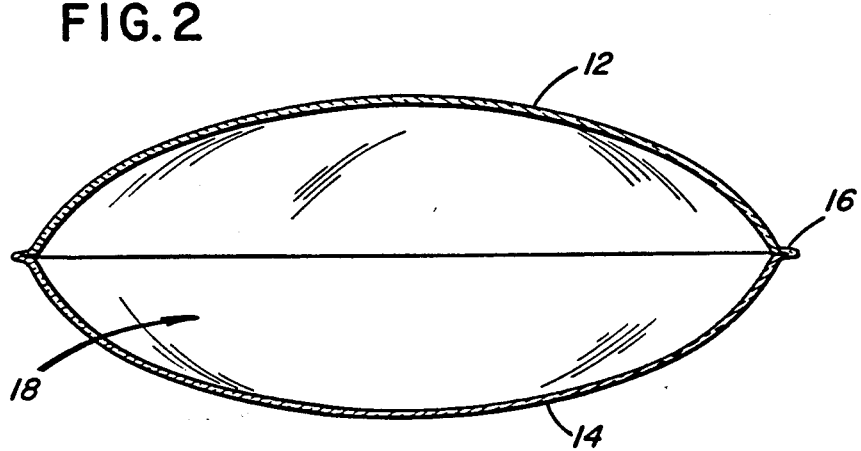
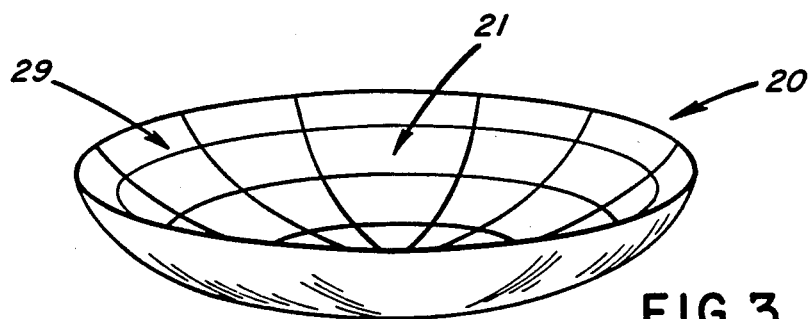
FIG. 3

FLUID LENS

RELATED INVENTIONS

This is a continuation in part of U.S. patent application Ser. No. 06/432,409 filed on Sept. 30, 1982, now U.S. Pat. No. 4,466,705.

BACKGROUND OF THE INVENTION

The present invention relates generally to an improved lens and, more particularly, to an improved lens which utilizes fluid, and particularly to fluid in the form of a hydrated hydrophilic polymer array, as its primary lens medium. The lens according to the present invention is especially suited for use as an intraocular lens.

It has long been recognized that ocular lenses made of glass or substantially rigid plastic result in irritation, discomfort and alteration of the normal corneal physiology. Therefore, attempts have been made to reduce these effects by using softer, more permeable lens materials, particularly in the area of contact lenses. For example, U.S. Pat. No. 2,241,415 to Moulton discloses an ophthalmic lens having a supporting portion formed of a thin, soft, pliable and slightly plastic material.

In recent years, so called "soft" contact lenses have been manufactured which utilize hydrogels as lens materials to reduce eye irritation and discomfort. For example, in U.S. Pat. No. 4,123,408, Gordon discloses a contact lens of a hydrogel composition wherein the hydrogel utilizes a polymerized water-insoluble, water-swellable polymer composition. U.S. Pat. No. 4,153,349 to Wichterle also discloses a method of making hydrogel contact lenses having improved lens properties. While "soft" contact lenses have reduced irritation and discomfort experienced while using prior art lenses, the soft contact lenses, while softer than prior art rigid lenses, must be sufficiently rigid to maintain the desired lens shape when utilized by the wearer and therefore a significant amount of foreign matter is introduced into the eye.

Any time foreign matter is introduced into the eye, there is a potential problem that irritation and discomfort will result even if the material is relatively soft. It will also hinder the passage of oxygen, nutrients, other gases and metabolites between cornea and tear film and thus potentially alter the normal physiology and clarity of the cornea. The ideal lens would utilize body fluids, such as lachrymal fluids, to form the desired lens and thereby completely eliminate the need for introduction of foreign material into the eye. However, since it is not possible to retain such fluid in a desired lens configuration, at least some type of structural member must be included to form the fluid into the shape of the lens.

Therefore, the use of fluid in connection with ocular devices has been generally relegated to purposes other than the formation of a primary lens medium. For example, U.S. Pat. No. 3,710,796 to Neefe discloses an ophthalmic dressing where a drug is impregnated into a transparent osmotic permeable material which serves to define the shape of the device. Diffusion of the drug out of its impregnated or dispersed state within this homogeneous polymer apparently determines the drug delivery rate. European Patent Application No. 32,517 published July 29, 1981 discloses a lens which permits the configuration of the device to a cornea by utilizing an insert filled with physiologically compatible fluid such as lachrymal fluid. However, the lens utilizes a soft contact material, not the fluid, as the primary lens medium.

SUMMARY OF THE INVENTION

It is an object of the present invention to provide a new and improved lens.

It is a further object of the invention to provide a new and improved lens which utilizes fluid as the primary lens medium.

It is an additional object of the present invention to provide a new and improved lens which utilizes fluid as the primary lens medium and is particularly suited for use as an ocular lens.

It is another object of the present invention to provide a new and improved lens which utilizes fluid as the primary lens medium while keeping the structural material which forms the fluid in the shape of a lens to a minimum.

It is yet another object of the invention to provide a new and improved lens which utilizes fluid in the form of a hydrated, hydrophilic polymer array as the primary lens medium.

It is still a further object of the present invention to provide a new and improved lens which utilizes a semipermeable membrane to maintain a fluid body in a desired lens shape.

It is yet a further object of the present invention to provide a new and improved lens which utilizes a semipermeable membrane to maintain a fluid body in a desired lens shape and which retains the desired shape as a result of a pressure differential existing across the membrane.

It is an additional object of the present invention to provide a new and improved lens which will permit the delivery of physiologically active agents.

It is a further object of the present invention to provide a new and improved lens which will permit the maximum exchange of gases, nutrients and metabolites between cornea, lachrymal fluid and the atmosphere, thus minimally compromising normal physiology.

Another object of the present invention is to provide a physiological lenticule capable of being introduced into the substance of the cornea with minimal disruption of its normal physiology while at the same time, altering significantly its shape and refractive power.

Additional objects and advantages of the present invention will be set forth in part in the description which follows and in part will be obvious from the description or can be learned by practice of the invention. The objects and advantages are achieved by means of the processes, instrumentalities and combinations particularly pointed out in the appended claims.

To achieve the foregoing and other objects and in accordance with its purpose, the present invention provides a device for forming a fluid lens when immersed in a liquid medium. The device includes a semipermeable transparent sheath defining a fully enclosed cavity and having a plurality of pores for permitting a liquid to flow into the cavity. A hydrophilic polymer array is disposed in the cavity and presents a pressure differential across the sheath when the sheath is immersed in the liquid medium for causing liquid medium to flow into the cavity and to hydrate the array, causing the array to expand and to completely fill the cavity, thereby causing the sheath to expand and to assume a defined lenticular shape, wherein the hydrated array assumes a shape having an outer contour defined by the expanded sheath and constitutes a fluid lens.

Another aspect of the invention is to provide a lens comprising a semipermeable transparent sheath having a plurality of pores therein and including opposite anterior and posterior portions each having a peripheral edge, the edges being joined together to form a closed interior space between the portions, and a hydrophilic polymer array disposed in the interior space of the sheath and being hydrated by a liquid which enters the interior space of the sheath through the pores, the hydrated array filling the interior space of the sheath and constituting a fluid lens having anterior and posterior surfaces bounded and defined by the anterior and posterior portions of the sheath, respectively.

The present invention further provides a method of locating an intraocular lens into an eye comprising the steps of: providing a lens forming device comprising a semipermeable transparent sheath defining a fully enclosed cavity and having a plurality of pores for permitting a liquid to flow into the cavity, and an at least partially dehydrated, hydrophilic polymer array disposed in the cavity and presenting a pressure differential across the sheath when the sheath is located in the eye of a wearer of the lens causing a physiological liquid present in the eye of the wearer to flow into the cavity and to hydrate the array, causing the array to expand and to completely fill the cavity, thereby causing the sheath to expand and to assume a defined lenticular shape, wherein the hydrated array assumes a shape having an outer contour defined by the expanded sheath and constitutes a fluid lens; making an incision for insertion of the lens forming device into the eye; and inserting the lens forming device into the eye whereby the physiological liquid present in the eye will flow into the cavity to hydrate the array to form a fluid lens.

While the present invention is particularly suited for an ocular lens, it is also suitable for any lens which is intended to be utilized in a fluid environment. In addition, the lens of the present invention permits the dispensing of physiologically active agents over a sustained period of time.

BRIEF DESCRIPTION OF THE DRAWINGS

FIG. 1 is a perspective view of a lens according to the invention.

FIG. 2 is a sectional view along the section line II—II in FIG. 1.

FIG. 3 is a perspective view of an alternative embodiment of a lens in accordance with the invention.

DESCRIPTION OF THE PREFERRED EMBODIMENTS

Figure 4:
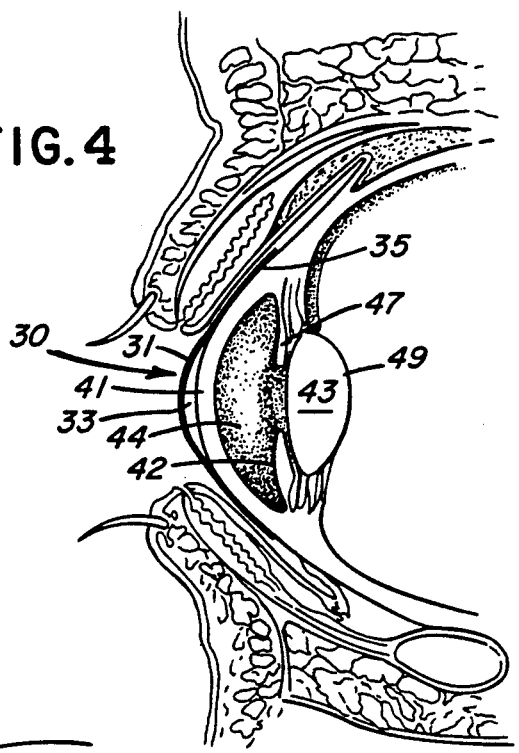
FIG. 4 is a sectional view of the alternative embodiments of the lens shown in FIG. 3 in place on the cornea of the wearer.

In accordance with the invention, as shown in FIG. 1, a lens 10, which is generally of circular configuration, consists of a body of fluid 19 which is bounded by two transparent thin sheets 12 and 14. The transparent thin sheets 12 and 14 are bound along their respective edges to form a sheath with an outside edge 16 which serves to retain the body of fluid 19. In accordance with the invention, the body of fluid comprises the primary lens medium of the present invention. The primary function of the transparent thin sheets 12 and 14 is not to constitute part of the lens medium, but is to retain the body of fluid 19 in a shape that will enable it to serve as the primary lens medium. As will be apparent hereinafter, the lens according to the invention, is intended to be used in a fluid environment with sufficient fluid present to enable the lens to operate as intended. The body of fluid 19 retained by the sheath formed by the thin transparent sheets 12 and 14 will not necessarily be present when the lens is not being used in its intended environment.

As can be seen in FIG. 2, transparent, thin sheets 12 and 14 define a cavity 18 which is intended to be filled by the body of fluid 19 which will constitute the lens medium. Thin transparent sheets 12 and 14 are provided with a plurality of pores in order to be semipermeable and permit the passage of fluid therethrough. The semipermeable thin transparent sheets 12 and 14, when joined to form edge 16 result in a semipermeable sheath.

According to the invention, cavity 18 will contain at least one macromolecule which will go into solution with the fluid in cavity 18 and the macromolecule along with the fluid in cavity 18 will form the body of fluid 19 which constitutes the lens medium. As will be described in more detail hereinafter, the term macromolecule is intended to mean a large molecule such as a protein, carbohydrate, rubber, or other natural or synthetic high polymer, or a polymer array, preferably a hydrophilic polymer array, commonly referred to as a hydrogel.

The presence of a macromolecule in cavity 18 will create a pressure differential across the semipermeable membrane which will cause fluid in the fluid environment in which the lens is used to flow into cavity 18. The pressure differential is due at least in part to the difference in molecular concentration being present across the semipermeable membrane which creates an osmotic pressure. When the macromolecule comprises a hydrophilic polymer array according to a preferred embodiment of the invention, molecular forces imparted by the hydrophilic nature of the macromolecule also contribute to the pressure differential across the semipermeable membrane for causing fluid medium to flow into cavity 18.

As indicated above, the presence of a macromolecule in solution in the body of fluid 19 results in a molecular concentration gradient being set up between the body of fluid 19 and the fluid environment in which the lens is used. This molecular concentration gradient will result in a net flow of fluid from the fluid environment through the semipermeable sheath into cavity 18. This flow of fluid, generally referred to as osmotic flow, results from the higher molecular concentration or higher osmotic pressure which is present in cavity 18 due to the presence of a macromolecule. That is, the body of fluid inside the semipermeable sheath is hypertonic with respect to the fluid outside of the semipermeable sheath, i.e. the fluid inside the semipermeable sheath has a higher osmotic pressure than the fluid outside the semipermeable sheath.

To assure that this concentration gradient is maintained, the macromolecule and semipermeable sheath are selected such that the macromolecule will not flow out of cavity 18 through the semipermeable sheath, yet the semipermeable membrane will permit the flow of fluid from the environment in which lens 10 is used into cavity 18. Because the macromolecule cannot leave cavity 18, the molecular concentration inside cavity 18 and the molecular concentration outside cavity 18 will never equalize. Since normally, osmotic flow will continue until the molecular concentrations are equalized, there is always a tendency for the surrounding fluid to flow through the semipermeable sheath.

Since the size of cavity 18 is determined by the sheath, and the tensile strength of the sheath is stronger than the pressure exerted due to the molecular concentration differences and any pressure due to the hydrophilic nature of the macromolecule, cavity 18 will always remain full.

When the present invention is employed as an ocular lens, the surrounding fluid environment will generally consist of lachrymal fluid and cavity 18 will fill with lachrymal fluid which will make up the body of fluid 19. As an intraocular lens, aqueous humor will surround the lens and be at an equilibrium with the intralenticular fluid. As an intracorneal lens, the interstitial fluid of the cornea will comprise fluid 19.

The osmotic flow which results due to molecular concentration differences is independent for each molecule involved. For example, in the above example if the macromolecule, designated A, and another molecule, designated B, were added to cavity 18, and went into solution and became part of the body liquid 19, molecule B would set up a concentration gradient across the semipermeable sheath independent of the gradient present as a result of macromolecule A. The osmotic flow resulting from the presence of molecule B would be independent of that occurring due to the presence of macromolecule A.

The present invention can be utilized for the delivery of physiological agents by incorporating such agents within cavity 18 and selecting the active agent such that it has a molecule size sufficiently small to pass through the semipermeable sheath. Preferably, a second macromolecule would be tagged with the physiological agent and the macromolecule selected such that it would be larger than the pores of the semipermeable sheath, yet it would decay over a period of time thereby allowing the active agent to slowly disperse from the semipermeable sheath. All the while, however, the first macromolecule, which is larger than the pore size of the semipermeable sheath, is confined within cavity 18. Because of the osmotic pressure generated by the first macromolecule, as soon as any active agent leaves the cavity, the surrounding fluid will still enter cavity 18 and maintain its configuration.

The macromolecule, according to the invention, should generally be photostable and inert to assure proper performance of the lens. The macromolecule may be selected from any class of compounds with molecular weight and configuration sufficiently large to be excluded passage by the desired pore size. Generally suitable are the dextrans, amylopectins (hydroxyethylstarch), polyvinylpyrrolidone, polyethylene glycol and various other soluble polymers, proteins and/or physiologically active agents. Also suitable are hydrogels including various cross-linked polymer and copolymer arrays of, for example, poly (2-hydroxymethyl methacrylate), polyvinylpyrrolidone, meythyl methacrylate, plus or minus cross-linking agents such as ethylene dimethacrylate and glyceryl methacrylate.

The active agents suitable for use in connection with the lens of the present invention include for example: oxygen, preferentially bound to fluorocarbons; salicylates, catechols, halogens, barbiturates or other compounds complexed to a macromolecule such as polyethylene glycols; antibiotics such as chloramphenicol, sulfa or other medications complexed with a macromolecule such as polyvinylpyrrolidone; antihistamines, quinine, procaine or other compounds complexed to a macromolecule such as sodium carboxymethylcellulose; salicylates complexed to the antibiotics oxytetracycline or tetracycline or other compounds complexed to a macromolecule such as salicylates or other macromolecules could be utilized such as caffeine or albumin as well as hydrogels such as those noted above. The above identified complexes have well known association constants. See generally *Remington's Pharmaceutical Sciences*, 16th Edition, Arthur Osol, Editor, Mack Publishing Co. 1980, pp. 182-193 and *Physical Pharmacy*, 2nd Edition, Martin et al, Lea & Febiger, 1969, pp. 325-352.

A given delivery rate of active agent and/or complexing molecule can be achieved through selection of appropriate membrane pore size, density and environmental conditions. Active agent and binding molecule form a molecular complex with an affinity for each other which can be expressed as an association constant, an easily determined quantity related to concentration and physicochemical environment. This constant is directly proportional to the concentration of the complex and inversely proportional to the product of the concentrations of active agent uncomplexed and binding molecule uncomplexed. It can thus be seen that if a nondiffusable binding molecule is chosen, the further dampening of a potentially rapid or exponential rate of delivery of active agent can be achieved.

The thickness of the semipermeable sheet material, utilized in connection with the invention, will depend on a number of factors and is directly related to the intended use of the lens. Generally, when concerned with ocular lenses, the membrane thickness will range from 5-10 micrometers, depending upon the material used and the desired configuration and concentration gradient intended to be utilized. Sheet material could be selected from cellulose acetate, cellulose acetate butyrate, cellulose triacetate, poly-1,4-butylene terephthalate (such as MYLAR®), polymethylmethacrylate, polypropylene (such as CRYOYAC®), polystyrene, polyvinyl acetate, polyvinyl chloride, polyvinyl fluoride, polyvinylidene chloride (such as SARAN®) silicon-polycarbonate copolymers (such as NUCLEPORE®) and others.

The transparent sheets can be made porous in a variety of ways. For example, the technique of nuclear track etching can be used, in which the polymer films are exposed to radioactive decay particles and products and then treated chemically to "etch" permanently the tracks of the particles through the film, thus creating pores of a size and density determined by the exposure time and etching process. The particle dose determines the hole density while the pore diameter is a function of etching time. The specific particles, dose, etchants, and other conditions to achieve desired pore sizes and density for the aforementioned polymer films are well known in the prior art. See *Nuclear Tracks in Solids: Principles and Applications*, R.L. Fleischer et al, University of California Press, 1975. For example, polycarbonate filters (such as NUCLEPORE®) are produced by exposure to $U^{235}$ followed by sodium hydroxide etching. Polyvinylidene chloride (such as SARAN®) can be made microporous by exposure to fission fragments of Californium$^{252}$ followed by etching with potassium permanganate at 55 degrees Centigrade. As an alternative to nuclear tracking etching, the newer advanced lasers such as frequency-doubled Neodymium-YAG or tunable dye lasers may be used to produce pores of the desired size and density.

Pores may also be created by forming membranes as integrated sheets of polymer containing "pore-formers," molecules which subsequently can be leached or dissolved out, leaving a predictable pore size. The leaching or dissolution can be accomplished prior to use or so selected to occur in the environment of use. For example, certain polymer films made of various polycarbonates, polyamides, polyesters, including such pore formers as lithium carbonate, calcium phosphate, various polysaccharides such as mannitol, CARBOWAX®, etc. The microporous paths then fill with a medium, compatible with or, identical to the medium of the environment in which active agent, complexing (binding) molecule and complex are soluble, thus permitting diffusion of active agent and fluid medium out of compartment 18 and the generation of an osmotic gradient across semipermeable sheets 14, 16. These above processes, and others for creating microporous membranes, are noted in the prior art literature and are compiled in such works as *Synthetic Polymer Membranes* by R. E. Kesting, McGraw-Hill, Inc., 1971.

The pore size will preferably range between 50 Angstroms diameter to 1,000 Angstroms; however, it is possible to have pore sizes smaller than 50 Angstroms, if desired. The pore size is selected depending on the molecular weight of the macromolecule. For example, a pore size of approximately 60 Angstroms will exclude a molecule having a molecular weight of about 10,000. A 100 Angstrom pore size will exclude a molecule having a 100,000 molecular weight. The exact three dimensional configuration of the molecules may, of course, produce exceptions. Pore density would be on the order of $10^5$ to $10^{10}$ per square cm; however, depending on the application of the lens, pore densities less than $10^5$ per square cm may be used.

The thin transparent sheets 12 and 14 may be joined at their respective edges to form edge 16 in a variety of ways. Various heat and impulse sealers can be used with variations in temperature, frequency, and times allowing for substantial flexibility depending upon particular polymer. Various one-part and two-part compatible adhesive bonding systems such as EASTMAN 910®, EPON 828® and 3M CONTACT CEMENT® could also be used. In addition, some materials are suitable for bonding without using conventional bonding methods. For example vinylidene chloride may be sealed to itself while in the so-called "supercooled" state to form a strong bond without conventional dielectric heat or adhesive methods.

The refractive index of the lens will be determined by composition and concentration of the body of fluid 19 formed in cavity 18. For example, dilute solutions of dextran (average molecular weight 75,000) and amylopectin have a refractive index similar to that of plain water or saline solution, 1.336. (Amylopectin average molecular weight, 545,167). A 17% solution of this same dextran has a refractive index 1.3560, a 33% solution, 1.397 and a 50% solution of amylopectin has a refractive index of 1.432.

The fluid pressure within lens 10 is sufficient to assure that the body of fluid 19 will retain its proper shape yet not strong enough to burst the semipermeable sheath formed by thin transparent sheets 12 and 14. Fluid pressures for lenses in accordance with the invention will be significantly less than the burst strength of the semipermeable membranes. For example, the pressure generated by the macromolecule will be in the order of less than 0.34 atmosphere (5 pounds per square inch), while, for example, the burst strength of vinylidene chloride 1 mil thick is 30 pounds per square inch.

Turning now to FIGS. 3 and 4, there are shown lenses 20, 30 in accordance with the invention, in the form of a contact lens. Lens 20 of FIG. 3 is made of a thin transparent sheet 21 of semipermeable material as previously described. While the lens of FIG. 3 is an ocular contact lens having a generally circular configuration, the principles of the invention are equally applicable to lenses of other shapes or other uses. Furthermore, while the lenses shown in FIGS. 3 and 4 are hyperopic contact lenses, the present invention is likewise suitable for myopic contact lenses. As the anterior surface is regular and independent of the posterior curvature, it will neutralize corneal astigmatism and/or irregularity.

Lens 20 includes scaffolding 29 on the rear surface of the semipermeable sheet 21. The scaffolding 29 serves to give additional support to sheet 21. Scaffolding 29 comprises polymethylmethacrylate, polypropylene, cellulose acetate butyrate, hydroxymethylmethacrylate or other rigid, semirigid or soft polymer strands. Scaffolding 29, as shown in FIG. 3, is fish net in configuration; however, it may be a variety of designs such as concentric rings connected by radial spokes, arcuate crossing elements, radial strands, a mesh of criss-crossing meridional fibers, etc. In addition, while scaffolding 29 is shown in connection with contact lens 20 of FIGS. 3 and 4, it could also be used in connection with other lenses, in accordance with the invention, such as the lens shown in FIGS. 1 and 2. In addition, as was the case with the formation of the semipermeable sheath, the scaffolding may be joined to the lens by known prior art methods such as by heat impulse sealing, adhesives, or during the manufacturing of the semipermeable sheath.

Turning now to FIG. 4, lens 30 is shown, in place, on the cornea of the wearer. FIG. 4 shows a human eye including a cornea 41, iris 42, eye lens 43, anterior chamber 44, posterior chamber 47 and posterior capsule 49. Thin transparent sheet 31 rests on cornea 41 and retains a body of fluid 33 which functions as the primary lens medium. As described in connection with the embodiment of FIGS. 1 and 2, the body of fluid 33 contains a macromolecule and has a higher concentration than the surrounding ocular fluid, primarily lachrymal fluids. Because the body is of higher concentration than the surrounding body fluids, the cavity defined by the thin, transparent sheet 31 and the cornea 41 will remain filled with fluid. Instead of being provided with scaffolding for added support, contact lens 30 includes a larger diameter outer portion 35 made of soft permeable material which serves as a lens carrier to support contact lens 30. Alternatively, the lenses, according to the invention, could utilize both scaffolding and a lens carrier if desired.

Figure 5:
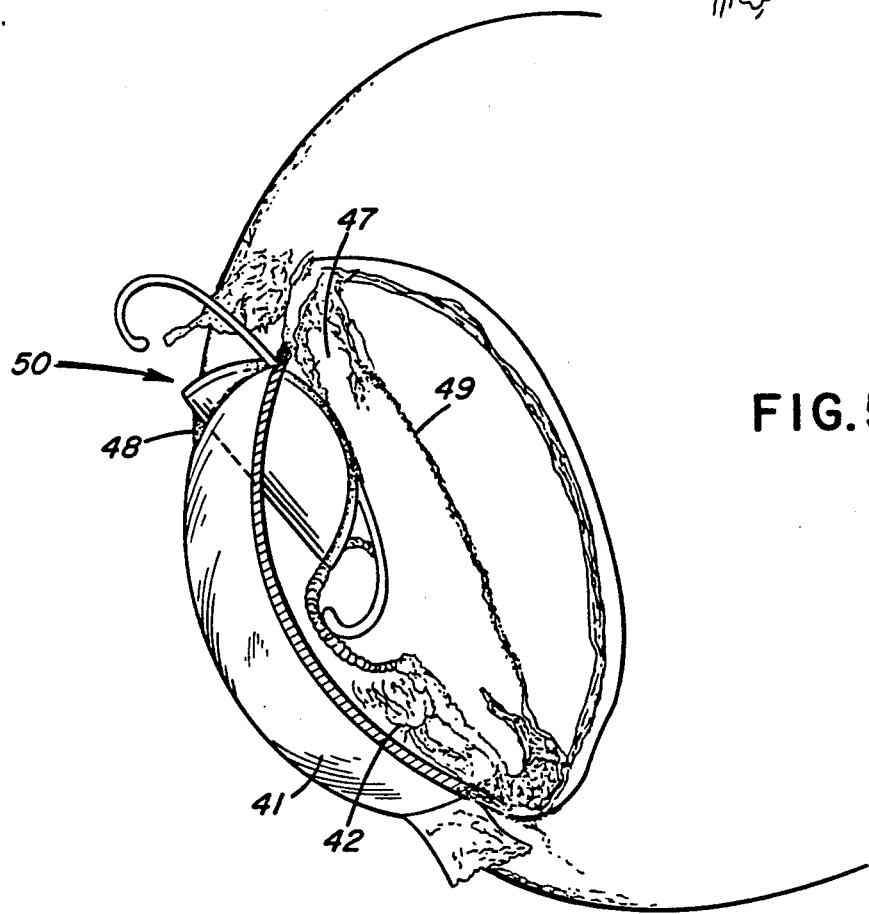
FIG. 5 is a perspective view of an eye in partial section showing an alternative embodiment of the invention partially inserted therein.

FIG. 5 shows an intraocular lens 50 in accordance with the invention partially inserted in the eye cavity. Lens 50 is provided with haptic support struts which serve to anchor the lens to the eye cavity. According to the method of the invention, because lens 50 is flexible and can be inserted in the eye in a dehydrated state, the lens may be folded or rolled to a size smaller than its hydrated size. This permits the use of a small incision as compared with prior art methods of insertion and results in lessened trauma to the patient. Once the dehydrated lens is inserted in the eye, it can be unfolded or unrolled and then permitted to hydrate in order to function as a lens.

The following specific examples of lenses constructed in accordance with the invention are set forth as illustrative only, and should not in any way limit the scope and purpose of the present invention.

EXAMPLE I

A contact lens according to the invention may be constructed for a moderately far-sighted patient after a cataract extraction, a moderately extreme example of need for hyperopic or "+" correction of +14.00 diopters. A semipermeable sheath of polyvinylidene chloride is provided which has been exposed to Californium 252 to create a pore density of about 10,000 pores per square cm and then etched in potassium permanganate at 55 degrees Centigrade for a time appropriate to create a pore diameter of 100 Angstroms. A refractive index of 1.366 is arbitrarily chosen and will require a solution of 20% amylopectin. A wide and generous optical zone of 7.0 mm is selected. The lens is designed to be fitted to a cornea so that its posterior radius will conform, for example, with an average 7.8 mm radius of the cornea. Given these parameters, an anterior curvature of the lens of 6.0 mm radius will occur and result in an extremely favorable thin lens having a central maximum thickness of the lens of 0.3 mm. The volume of the lens will be 6.19 mm$^3$ and thus 1.5 mg of amylopectin will create the desired 20% solution and refractive index of 1.366. The periphery of the lens can be heat-sealed at 225-260 degrees Fahrenheit. If necessary, a posterior scaffolding can be constructed of polymethylmethacrylate, a silicon polymethylmethacrylate polymer, polypropylene or hydrogel and joined to either posterior and/or anterior polymer films by heat impulse, compatible adhesive or the manufacturing process itself when mesh and/or film are in a precast state.

EXAMPLE II

A concave lens to correct high myopia, thus gaining "minus" power can be similarly constructed. For example a lens correcting relatively extreme myopia of −10.00 diopters, can be constructed. Assuming a cornea of average radius, 7.8 mm, choosing a refractive index for the lens of 1.366 equalling the index ascertained for a 20% solution of amylopectin, and a large optical zone of 7.0 mm diameter, the required anterior radius of the lens will be 9.9 mm. Given the basic stability and characteristics of this type of lens, it can be constructed with no significant center point thickness except for the thickness of the opposing membranes, thus attaining a maximum vertical height at its lateral thickest portion of 0.19 mm. The volume of this lens is 4.58 mm$^3$ and thus 1.1 mg of amylopectin will be added to the lens cavity. The osmotic pressure generated in the lenses is well below the burst strength of 30 pounds per square inch for a 1 mil film of polyvinylidene chloride.

EXAMPLE III

A lens for incorporation within the corneal substance (keratophakia) can be similarly constructed. The following conditions are assumed: an example of aphakic hyperopia; the need to generate a total ocular power from the posterior corneal surface of 60 diopters; an average normal anterior corneal radius of 7.8 mm; and a posterior corneal radius of 6.5 mm. As an extreme example, the lens may be made with a dilute solution of macromolecules such that the refractive index approaches that of water and aqueous humor and tears, namely 1.336, less than that of the cornea itself (1.376). A large optical zone of a diameter of 7.0 mm is chosen and a new anterior corneal radius of 5.6 mm is necessary. To achieve this change in corneal configuration, a lenticule, with an anterior radius of 5.35 mm, a posterior radius of 7.55 mm, thus generating a central maximum thickness of 0.4 mm, should be fabricated. Obviously, for increasing refractive index, a decreased thickness for any given diameter of optical zone can be achieved by requiring less of a change in the anterior convexity of the cornea. Reduction in corneal convexity, by incorporating minus concave lenses for the correction of myopia, can be similarly accomplished by fashioning such intrastromal lenticules as described for the contact lens. Support scaffolding can be incorporated into the anterior and/or posterior surfaces as needed. The periphery of this particular lens may be impulse sealed after incorporation of less than one-half mg of dextran (less than 5% solution), requiring a peripherally sealed zone of ½ to 1 mm for a total 8.0 to 9.0 mm diameter lenticule.

EXAMPLE IV

An intraocular lens may be constructed in accordance with the invention. Assuming an average intraocular lens power of 20 diopters, a lens symmetrically biconvex, and 33 ⅓% solution of dextran or amylopectin with a refractive index of 1.400, a generous optical zone for an intraocular lens of 6.0 mm diameter is chosen, thus requiring a radius anteriorly and posteriorly of 6.4 mm and creating a total thickness at the center maximum of 1.4 mm. The lens will have a volume of 11.92 mm$^3$ and thus require incorporation of 5.9 mg of Dextran or amylopectin. This lens may be constructed so that it has a ½ mm wide circumferential seal which incorporates thin support haptics enabling the lens in its dehydrated state to be folded or rolled and maneuvered into the eye through an incision 3 ½ to 4 mm long.

EXAMPLE V

A lens constructed for keratophakia can be constructed as in Example III with a hydrogel rather than a dilute solution of dextran as the internal fluid. A hydrogel of glyceryl methacrylate incorporating 97% water would have a refractive index of 1.336, and thus conform with all the other parameters of Example III.

Hydroxyethyl methacrylate hydrogels can be formulated to a refractive index dependent upon water content just as the refractive index of the solutions in any of the foregoing examples is dependent on concentration of polymer. For example, a known formulation of hydroxyethyl methacrylate having a refractive index 1.436 would allow the intraocular lens of Example IV to be constructed with a proportionately larger diameter if desired or a larger radius of curvature.

It is also possible to use a biodegradable polymer film to surround such hydrogel fluids. Upon complete hydration and stabilization, the hydrogel might no longer need a constricting and configuring sheath. Materials that may be used for such biodegradable sheaths include cellulose, collodion, polyvinyl pyrrolidone, polyamides, polylactide and polyglycolide.

It will be understood that the above description of the present invention is susceptible to various modifications, changes and adaptations, and the same are intended to be comprehended within the meaning and range of equivalents of the appended claims.

What is claimed is:

1. A device for forming a fluid lens when immersed in a liquid medium, comprising:
   a semipermeable transparent sheath defining a fully enclosed cavity and having a plurality of pores for permitting a liquid medium to flow into said cavity;
   a hydrophilic polymer array disposed in said cavity and presenting a pressure differential across said sheath when said sheath is immersed in the liquid medium for causing liquid medium to flow into said cavity and to hydrate said array, causing said array to expand and to completely fill said cavity, thereby causing said sheath to expand and to assume a defined lenticular shape, wherein said hydrated array assumes a shape having an outer contour defined by said expanded sheath and constitutes a fluid lens.

2. The device of claim 1 wherein said transparent sheath has a thickness of less than 50 microns.

3. The device of claim 1 wherein the liquid medium in which said lens is to be immersed comprises a physiological solution.

4. The device of claim 3 wherein said physiological solution comprises a physiological saline solution 5. The device of claim 3 including a physiologically active agent complexed to said array.

6. The device of claim 1 wherein said array is photostable.

7. The device of claim 1 wherein said array is inert.

8. The device of claim 1, wherein said sheath comprises two semipermeable transparent sheets each having a peripheral edge, said edges being joined together to form said cavity and further comprising scaffolding means attached to one of said sheets for maintaining said one sheet in a concave shape relative to said cavity.

9. A device according to claim 1, wherein said sheath is a biodegradable polymer film.

10. A lens comprising:
    a semipermeable transparent sheath having a plurality of pores therein and including opposite anterior and posterior portions each having a peripheral edge, said edges being joined together to form a closed interior space between said portions;
    a hydrophilic polymer array disposed in the interior space of said sheath and being hydrated by a liquid which enters the interior space of said sheath through said pores, said hydrated array filling the interior space of said sheath and constituting a fluid lens having anterior and posterior surfaces bounded and defined by said anterior and posterior portions of said sheath, respectively.

11. A method of locating an intraocular lens into an eye comprising the steps of:
    (a) providing a lens forming device comprising a semipermeable transparent sheath defining a fully enclosed cavity and having a plurality of pores for permitting a liquid to flow into the cavity and an at least partially dehydrated, hydrophilic polymer array disposed in the cavity and presenting a pressure differential across the sheath when the sheath is located in the eye of a wearer of the lens for causing a physiological liquid present in the eye of the wearer to flow into the cavity and to hydrate the array, causing the array to expand and to completely fill the cavity, thereby causing the sheath to expand and to assume a defined lenticular shape, wherein the hydrated array assumes a shape having an outer contour defined by the expanded sheath and constitutes a fluid lens;
    (b) making an incision for insertion of the lens forming device into the eye; and
    (c) inserting the lens forming device into the eye whereby the physiological liquid present in the eye will flow into the cavity to hydrate the array to form a fluid lens.

12. The method of claim 11 including folding the sheath prior to inserting it into the eye and unfolding the sheath after insertion into the eye.

13. The method of claim 12 wherein said making step includes making the incision only large enough to permit the insertion of the folded sheath.

* * * * *